United States Patent [19]

Shih et al.

[11] Patent Number: 4,897,397

[45] Date of Patent: Jan. 30, 1990

[54] ARYL-ALKYNOIC, ALKENOIC OR ALKANOIC COMPOUNDS AND COMPOSITIONS USEFUL AS ANTIALLERGY AND ANTI-INFLAMMATORY AGENTS

[75] Inventors: Neng Y. Shih, Cedar Grove; David J. Blythin, North Caldwell, both of N.J.

[73] Assignee: Schering Corporation, Kenilworth, N.J.

[21] Appl. No.: 285,894

[22] Filed: Dec. 16, 1988

[51] Int. Cl.[4] ................. C07D 277/28; C07D 277/22; C07D 277/42; A61K 31/44; A61K 31/425

[52] U.S. Cl. .................... 514/277; 514/317; 514/319; 514/327; 514/329; 514/331; 514/345; 514/351; 514/352; 514/357; 514/365; 514/369; 514/370; 514/374; 514/376; 514/377; 514/392; 514/396; 514/398; 514/400; 514/424; 514/426; 514/427; 514/428; 514/429; 514/432; 514/438; 514/444; 514/459; 514/460; 514/461; 514/471; 514/472; 514/473; 514/513; 514/557; 514/576; 546/205; 546/206; 546/217; 546/223; 546/224; 546/232; 546/233; 546/238; 546/300; 546/301; 546/312; 546/335; 546/342; 548/187; 548/194; 548/204; 548/228; 548/229; 548/234; 548/236; 548/315; 548/335; 548/337; 548/342; 548/346; 548/400; 548/541; 548/543; 548/557; 548/559; 548/560; 548/561; 548/562; 548/566; 548/570; 548/577; 549/13; 549/28; 549/62; 549/65; 549/66; 549/68; 549/77; 549/79; 549/416; 549/424; 549/426; 549/427; 549/475; 549/479; 549/480; 549/494; 549/496; 549/498; 549/499; 560/15; 560/19; 560/55; 560/57; 560/59; 560/60; 560/100; 560/101; 560/102; 562/426; 562/427; 562/465; 562/466; 562/468; 562/469; 562/471; 562/490; 562/491; 564/162; 564/163; 564/181; 564/189; 564/204

[58] Field of Search ............... 514/277, 317, 319, 327, 514/329, 331, 345, 351, 352, 357, 365, 369, 370, 374, 376, 377, 392, 396, 398, 400, 424, 426, 427, 428, 429, 432, 438, 444, 459, 460, 461, 471, 472, 473, 513, 557, 576, ; 546/205, 206, 217, 223, 224, 232, 233, 238, 300, 301, 312, 335, 342; 548/187, 194, 204, 228, 229, 234, 236, 315, 335, 337, 342, 346, 400, 541, 543, 557, 559, 560, 561, 562, 566, 570, 577; 549/13, 28, 62, 65, 66, 68, 77, 79, 416, 424, 426, 427, 475, 479, 480, 494, 496, 498, 499; 560/15, 19, 55, 57, 59, 60, 100, 101, 102

[56] References Cited

U.S. PATENT DOCUMENTS 4,405,810   9/1983   Blythin et al. ................. 562/495
4,528,392   7/1985   Musser et al. ................. 560/43

FOREIGN PATENT DOCUMENTS 110405   6/1984   European Pat. Off. .

Primary Examiner—Richard A. Schwartz
Assistant Examiner—Richard A. Sharpe
Attorney, Agent, or Firm—Gerald S. Rosen; James R. Nelson; Stephen I. Miller

[57] ABSTRACT

Certain aryl-alkynoic, alkenoic and alkanoic acids and derivatives and their use in treating inflammation, allergy and hyperproliferative skin disease are disclosed.

18 Claims, No Drawings

ARYL-ALKYNOIC, ALKENOIC OR ALKANOIC COMPOUNDS AND COMPOSITIONS USEFUL AS ANTIALLERGY AND ANTI-INFLAMMATORY AGENTS

BACKGROUND OF THE INVENTION

The present invention relates to certain aryl-alkynoic, alkenoic and alkanoic acids and derivatives and their use in pharmaceutical compositions and in methods of treating inflammation, allergy and hyperproliferative skin disease.

European published patent Application No. 0 110 405 discloses compounds of the formula

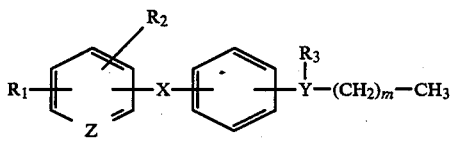

and pharmaceutically accepted salts thereof, wherein $R_1$ and $R_2$ are independently hydrogen, alkyl, carboxy, alkanoyloxy, aroyloxy, carboxyalkyl, carbalkoxyalkyl, carbalkoxy, alkanoyl, formyl, nitrile, amino, aminoalkyl, alkylamino, carboxamide, halo, trihalomethyl, hydroxy, aryloxy, nitro, sulfamyl, thio, alkylthio, and R1 and R2 when taken together with the carbon atoms to which they are attached form a phenyl ring;

Z is C or N,

X is —O—, S—, NR₄, —CH₂Z₁—, —CH=N—, —CH=CH—, —C≡C—, —C=O, —CH₂ZCH₂—, —CH=CH—, —CH₂CHR₅— or —CH(C(R₅)₃)₂— when R₃ is monovalent or —C—CH₂— when R₃ is O;

R₃ is O, OH, OR₄, SH, SR₄, NH₂, HNR₄ or N(R₄)₂; and m is an integer from 0 to 10; wherein Z₁ is O, S or NR₄; R₄ is H, alkyl, pyranyl or aryl; and R₅ is H or alkylfluoro. These compounds are said to have antiinflammatory and antiallergic activities.

Blythin U.S. Pat. No. 4,405,810 discloses certain 7-arylhept-5-ynoic acids and derivatives thereof and indicates that such compounds have antiallergy and antiinflammatory activities.

Musser et al. U.S. Pat. No. 4,528,392 discloses compounds of the formula

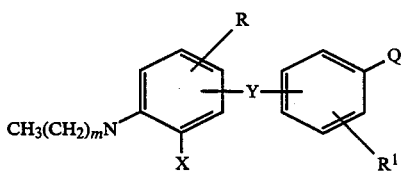

wherein
X is OR², SR², N(R²)₂ or halo;
N is —CH₂—, —C(O)—, —CH(OH)— or —CH(OR)—
Y is —CH₂O—, —OCH₂—, —CH₂S—, —SCH₂, —CH₂—N(R²)—, —N(R²)—CH₂—, —C(O)—N(R²)—, —N(R²)—C(O)—, —O—, —S— or —N—;
Q is Z—(CH₂)ₙ—C(A)—B;

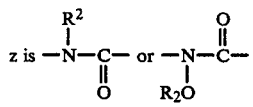

m is 0–6;
n is 0–6;
p is 1–3;
A is O or S;
B is OR², SR² or N(R²)₂;
R¹ is hydrogen, loweralkyl, loweralkoxy or halo;
R² is hydrogen or lowerlakyl; and the pharmaceutically acceptable salts thereof, and their use in the treatment of leukotriene-mediated nasobronchial obstructive air passageway conditions, such as allergic rhinitis, allergic bronchial asthma and the like.

SUMMARY OF THE INVENTION

It has now surprisingly been found that compounds of the formula I below provide anti-allergy and antiinflammatory activities and are useful in the treatment of hyperproliferative skin disease:

$$R_4(CHR^3)_m\text{-}Y\text{-}Ar\text{-}X\text{-}(CR^5R^6)_n\text{-}COR^1 \quad 1$$

or a pharmaceutically acceptable salt thereof, wherein m represents an integer of from 0 to 4;
n represents an integer of from 2 to 6:
Ar represents

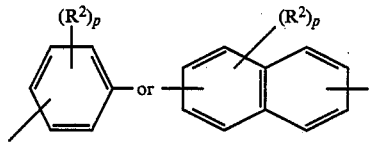

p is 0, 1 or 2;
X represents —C≡C—, —CH=CH— or —CH₂—CH₂—
Y represents O, S, NR⁷ or a covalent bond;
R¹ represents alkoxy, OH or N(R⁷)₂;
each R² independently represents a substituent selected from halo, alkyl, alkoxy, CN, OH, NO₂, CF₃ or cycloalkyl;
R³ represents H, alkyl, alkenyl, alkynyl, alkoxy, or alkylthio, with the proviso that if Y is O, S or NR⁷, R³ is not alkoxy or alkylthio on the carbon atom adjacent to Y;
R⁴ represents H, alkyl, alkenyl, alkynyl or a cyclic group selected from:

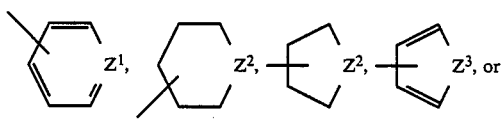

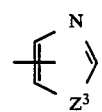

wherein Z¹ is N, CH or CR², Z² is CHR⁷, O, S or NR⁷ and Z³ represents NR⁷, S or O;

$R^5$ and $R^6$ may be the same or different and each independently represents H, alkyl, alkoxy, or alkylthio, with the proviso that $R^5$ and $R^6$ are not both alkoxy and/or alkylthio on the same carbon atom; and each $R^7$ is independently selected from H or alkyl.

Thus, the invention also includes the use of the compound of formula I in pharmaceutical compositions in combination with a pharmaceutically acceptable carrier and in methods of treating mammals for allergy, inflammation and hyperproliferative skin disease.

In the compounds of formula I, $R^4$ is preferably one of the cyclic groups as defined above, and more preferably is phenyl or imidazoyl. $R^2$ is preferably H, OH, alkoxy or halo. Preferably, $R^5$ and $R^6$ are preferably independently selected from H or alkyl. More preferably, $R^5$ and $R^6$ are both H. n preferably represents an integer from 2 to 4, more preferably 3. m is preferably 0, 1 or 2. $R^3$ is preferably H or alkyl. X is preferably —HC=CH— and Y is preferably O.

A preferred embodiment of the invention involves compounds of the formula If

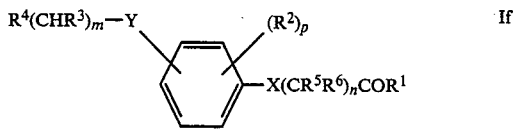

wherein m, n, p, X, Y, $R^1$, $R^2$, $R^3$, $R^4$, $R^5$ and $R^6$ are as defined above.

DETAILED DESCRIPTION OF THE INVENTION

The compounds of formula I contain a —$(CR^5R^6)_n$— substituent wherein each $R^5$ group and each $R^6$ group may vary independently. Thus, for example, when n equals 2, the following patterns of substitution (wherein hydrogen and $CH_3$ are used to represent any substituent, $R^5$ or $R^6$) are contemplated: —$CH_2CH_2$—, —$CH(CH_3)CH_2$—, —$CH_2CH(CH_3)$—, —$C(CH_3)_2CH_2$—, —$CH_2C(CH_3)_2$—, —$(C(CH_3)H)_2$—, and the like. In the same manner, each $R^3$ in the group —$(CHR^3)_m$— may vary.

As noted above, the compounds of the invention may include one or two $R^2$ substituents on the Ar group, i.e., $R^2$ replaces an H on the Ar ring system. In compounds where there is more than one such $R^2$ substituent, they may be the same or different. Thus, compounds having combinations of different $R^2$ substituents are contemplated within the scope of the invention. Examples of suitable $R^2$ substituents include hydroxy, methyl, chloro, bromo, methoxy, cyclohexyl, and the like.

The Ar group represents

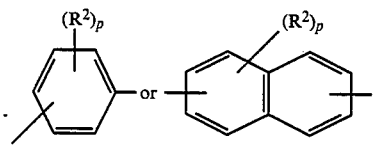

The bonds to the groups Y and X and to the substituent(s) $(R^2)_p$ are thus intended to be attached at any of the available carbon atoms of the phenyl or naphthyl rings. In the same manner, the bond of the cyclic groups $R^4$ to $(CHR^3)_m$ may be attached at any of the available carbon atoms of the cyclic group.

Compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of this invention.

Certain compounds of the invention may exist in isomeric forms. The invention contemplates all such isomers both in pure form and in admixture, including racemic mixtures.

Certain compounds of the invention also form pharmaceutically acceptable salts with organic and inorganic acids, e.g., those containing an $NR^7$ group. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia or sodium bicarbonate. The free base forms differ from their respective salt forms somewhat in certain physical properties, such as solubility in polar solvents, but the salts are otherwise equivalent to their respective free base forms for purposes of the invention.

Also, some compounds of this invention are acidic, e.g., when $R^1$ is OH, and can form salts with inorganic and organic bases. Suitable basic salts include, for example, sodium, potassium, calcium, aluminum, gold and silver salts. Also contemplated are salts formed with ammonia or pharmaceutically acceptable organic amines such as alkyl amines, hydroxyalkylamines, N-methylglucamine and the like.

Unless otherwise indicated, the terms listed below have the following means:

alkyl (including the alkyl portions of alkoxy and alkylthio)—a straight or branched hydrocarbon chain having from 1 to 12 carbon atoms, preferably from 1 to 6 carbon atoms;

alkenyl—a straight or branched hydrocarbon chain containing at least one carbon-carbon double bond and having from 2 to 12 carbon atoms, preferably from 2 to 6 carbon atoms, e.g., allyl;

alkynyl—a straight or branched hydrocarbon chain containing at least one carbon-carbon triple bond and having from 2 to 12 carbon atoms, preferably from 2 to 6 carbon atoms, e.g., —C≡CH; cycloalkyl—a saturated carbocyclic ring containing from 3 to 8 carbons, e.g., cyclohexyl or cyclopentyl; and halo—fluoro, chloro, bromo or iodo.

The compounds of the invention may be prepared by the processes described in sections A–E below, wherein m, n, p, Ar, X, Y, $R^1$, $R^2$, $R^3$, $R^4$, $R^5$ and $R^6$ are as defined above, unless otherwise indicated. Also, unless otherwise indicated, Ph represents a phenyl ring and Ar represents an aryl group as defined above.

A. A compound of formula II may be reacted with a compound of formula III to produce a compound of formula Ia″ wherein R4a represents $R^4$ with the exception of imidazoyl.

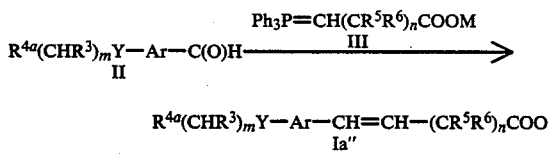

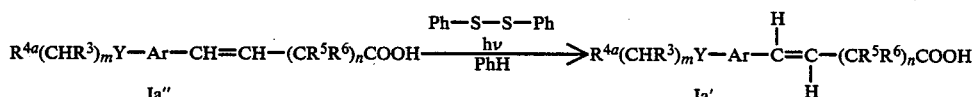

The above reaction of Compound II with III can be carried out at any suitable temperature, e.g., 0° C. to about room temperature, in a polar organic solvent. Suitable organic solvents include tetrahydrofuran (THF).

The pure trans olefin Ia' can be obtained by irradiation of Ia" with light in the presence of Ph—S—S—Ph (where Ph represents a phenyl group).

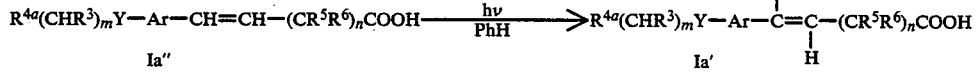

The carboxylic acid of formula Ia' can be converted to the corresponding acid chloride by reaction with oxayl chloride in an organic solvent such as $CH_2Cl_2$ at about room temperature, in the presence of a catalytic amount of DMF. This is followed by reaction with $R^1H$ to give Ia.

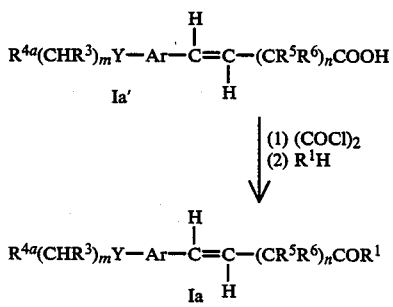

Compound III (where M is a metal cation such as Li or K) can be prepared from IIIa by reacting it with a strong base in an organic solvent at a suitable temperature, preferably from about 0° C. to about room temperature. Preferred strong bases are lithium diisopropylamide or potassium hydride and a preferred organic solvent is THF.

The compounds of formula II may be prepared by at least two methods. In one such method, a compound of formula IV is reacted with a compound of formula Va in the presence of a strong base such as NaH in an organic solvent, e.g., dimethylformamide (DMF):

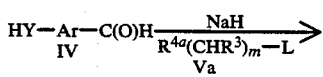

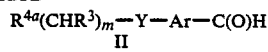

wherein L is a suitable leaving group such as chloro, bromo, iodo, tosyl and the like.

Alternatively, a compound of formula II may be prepared by the following reaction scheme:

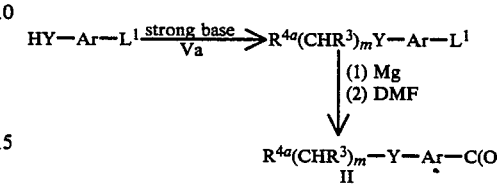

wherein $L^1$ is a suitable halo group such as bromo or iodo.

The compounds of formula IV and Va are either commercially available (for example, from Aldrich or Lancaster) or easily made by well known methods conventional in the art.

B. A compound of formula Ib wherein $R^{4b}$ is imidazoyl and $R^{1b}$ is alkoxyl, may be prepared by reacting a compound of formula VI with a compound of formula Vb in the presence of a base such as sodium ethoxide (when $R^{1b}$ is ethoxyl):

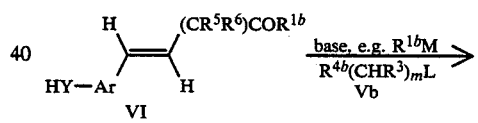

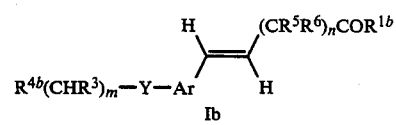

wherein M is a counterion such as Na or Li and L is a leaving group as described above.

The reaction solvent is a polar protic solvent, for example ethanol, and any suitable reaction temperature may be employed preferably about room temperature.

Compound Ib may then be converted to Ic by the following sequence:

First, hydrolysis of Ib to carboxylic acid Ic', which then may be converted to Ic according to the same method described previously as Ia' to Ia:

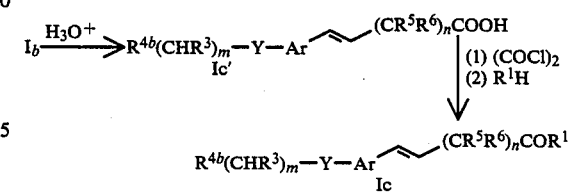

The compounds of formula VI may be prepared by the following reaction scheme:

The compounds of formula VII may be prepared by the following reaction scheme:

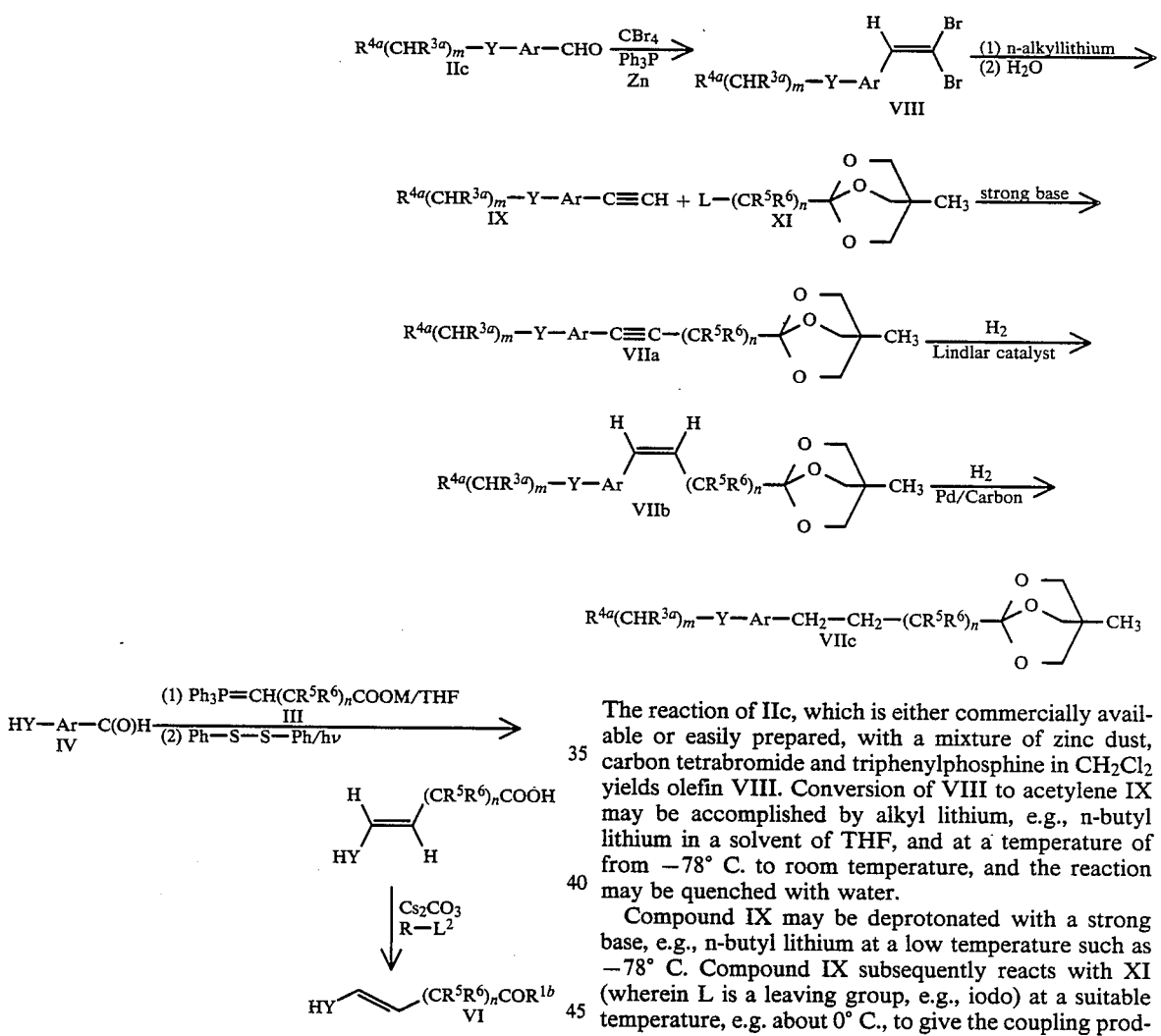

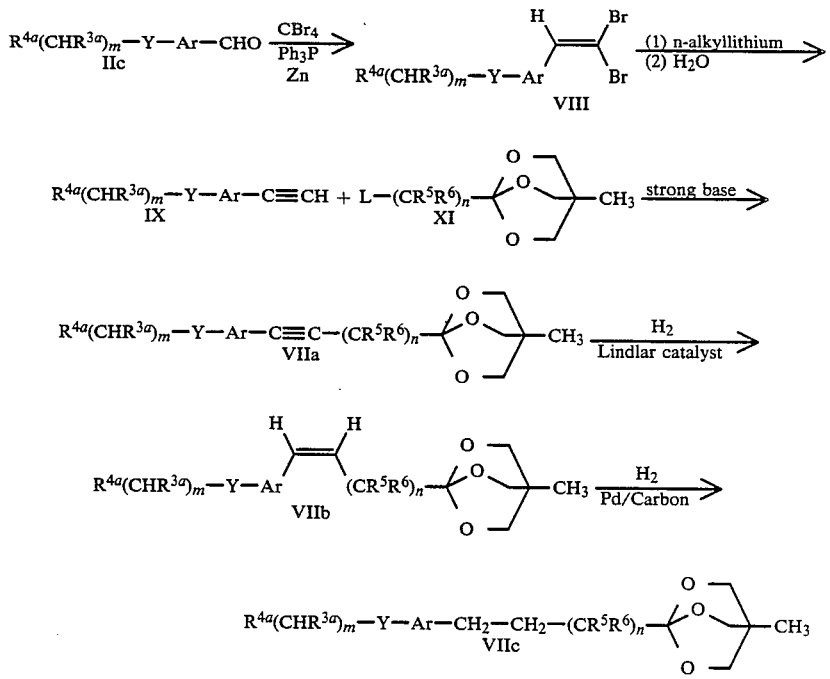

The reaction of IIc, which is either commercially available or easily prepared, with a mixture of zinc dust, carbon tetrabromide and triphenylphosphine in $CH_2Cl_2$ yields olefin VIII. Conversion of VIII to acetylene IX may be accomplished by alkyl lithium, e.g., n-butyl lithium in a solvent of THF, and at a temperature of from $-78°$ C. to room temperature, and the reaction may be quenched with water.

Compound IX may be deprotonated with a strong base, e.g., n-butyl lithium at a low temperature such as $-78°$ C. Compound IX subsequently reacts with XI (wherein L is a leaving group, e.g., iodo) at a suitable temperature, e.g. about $0°$ C., to give the coupling product VIIa. Reduction of VIIa under hydrogen with a Lindlar catalyst at room temperature in the presence of an amine base (for example, triethylamine) results in a cis olefin compound of the formula VIIb. Compound VIIc may be obtained by further hydrogenation using Pd/carbon as a catalyst.

Compound XI can be prepared according to the procedure described in Tet. Let., Vol. 24, No. 50, p. 5571 (1983).

Isomerization of VIIb according to the method described above for the conversion of Ia" to Ia', can yield the trans olefin VIId.

wherein M is a suitable counterion and $L^2$ is a suitable leaving group such as iodine and R is an alkyl group. The reaction solvent for the conversion of COOH to $-COR^{1b}$ is a polar aprotic solvent, e.g., DMF, at any suitable reaction temperature, preferably about room temperature.

C. A compound of formula Id' wherein $R^{3a}$ is $R^3$ except for alkenyl or alkylnyl, $R^{4a}$ and Y are as defined above, and X is $-C\equiv C-$, $-CH=CH-$ or $-CH_2-CH_2-$ may be prepared by reacting a compound of formula VII with a strong acid such as $NaHSO_4$ and a suitable base MOH, such as LiOH:

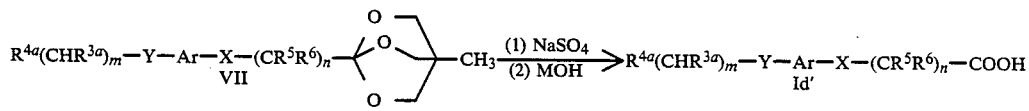

wherein M is as defined above. The solvent for this reaction is a suitable organic solvent, preferably a mixture of dimethoxyethane (DME) and water and the

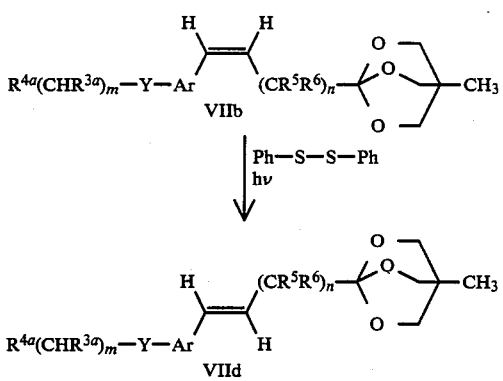

Compound Id' can be converted to Id according to the same method as that described for the convertion of Ia' to Ia (above). Compound Id, when $R^1$ is alkoxy, can alternatively be prepared by reacting Id' with $R^{1b}$—L in the presence of a base such as $K_2CO_3$.

formula V in the presence of a suitable base such as NaOEt (when $R^4$ is imidazoyl) or NaH (when $R^4$ is not imidazoyl).

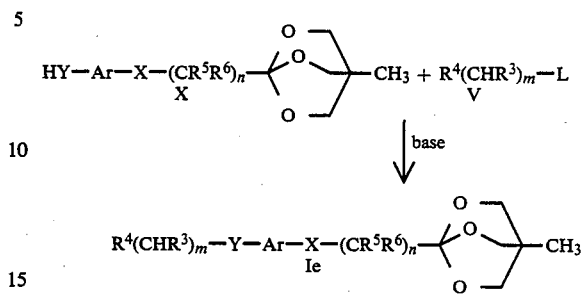

Acid hydrolysis, as described for the conversion of VII to Id' above, can be used to convert compound Ie to compound If'. Compound If' may then be converted to If by the same method of converting compound Ia' to Ia as described above.

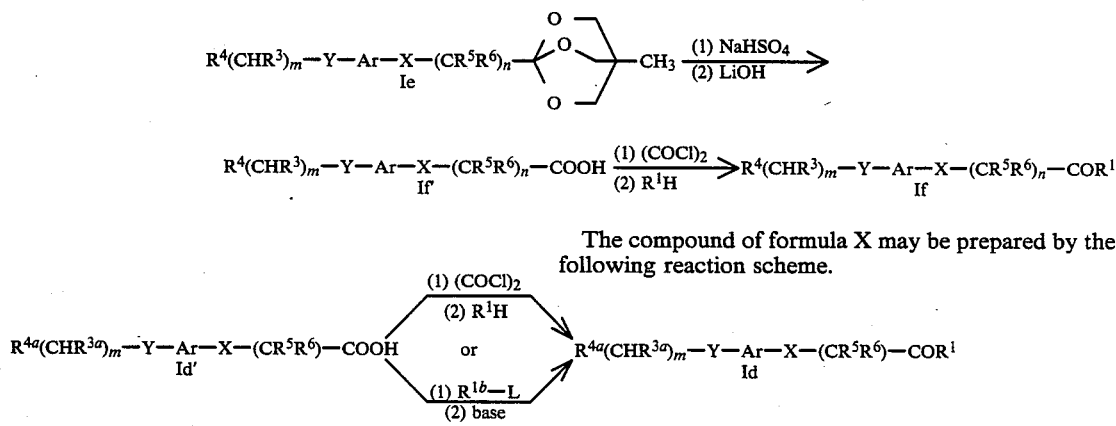

The compound of formula X may be prepared by the following reaction scheme.

D. Compounds of formula Ie can be prepared by reacting a compound of formula X with a compound of

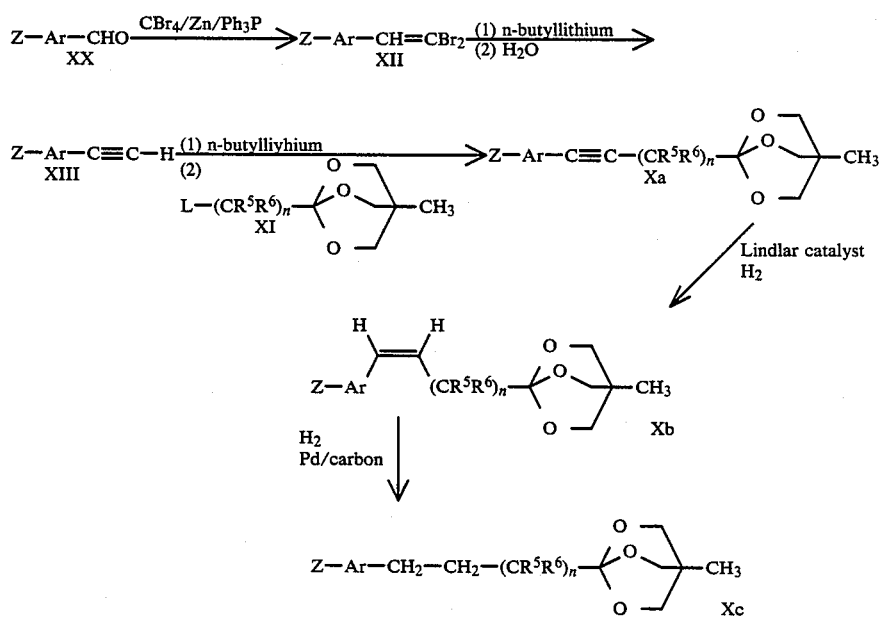

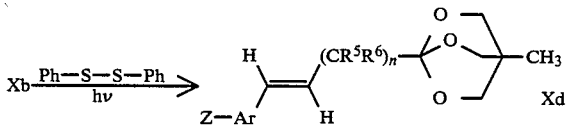

In compounds of formula XX, Z is YH or a suitable Y protecting group. For example, a suitable Y protecting group is tetrahydropyran when YH is OH. The reaction conditions for the above reaction scheme are essentially the same as those utilized for the preparation of compound VII as described above.

E. Compound Xa may be prepared by the palladium catalyzed coupling of XVI with XVII.

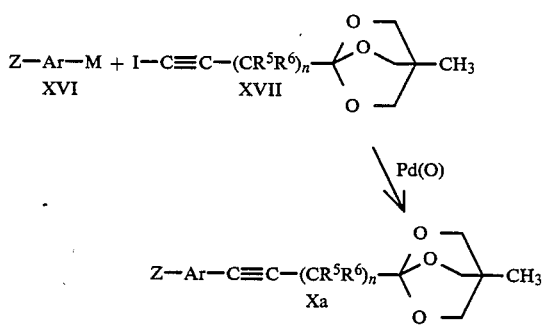

In compound XVI, Z is YH or the protected Y, for example, Z is O-2-tetrahydropyranyl, N-2-tetrahydropyranyl or S-benzyl thioether. M is a metal such as Li, ZnCl or MgBr and the palladium catalyst is Pd(PPh3)4 or Pd(PPh3)2Cl2, wherein Ph represents a phenyl group, as described in Sakamato et al., Chem. Pharm. Bull. 36(4): 1305 (1988). The solvent for the reaction is a common organic solvent, e.g., THF, DMF or the like. The compounds of formula Xa can be converted to compounds of formula 1 above by appropriate deprotection and the other reactions as described above.

Compound XVI can be prepared from XVIII wherein X is bromo or iodo, by reacting it with metal M, wherein M represents, for example Li or Mg. The reaction is run in an organic solvent preferably THF or ethyl ether.

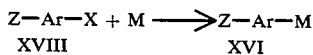

Compound XVII may be prepared from the known compound XIX [Tet. Lett., Vol. 24, P. 5571 (1983)] by sequentially reacting it with BuLi, then iodine.

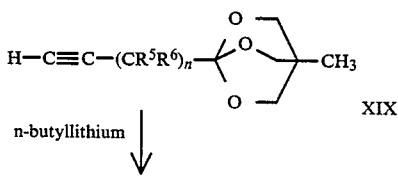

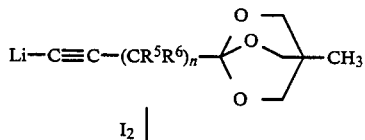

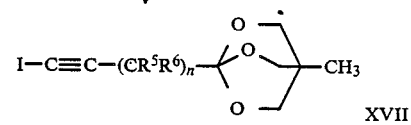

The reaction can be carried out at suitable low temperature, preferably about −78° C., in a suitable organic solvent, which is preferably THF. The conversion of compound Xa to If is accomplished as described in part D above.

The compounds of this invention inhibit 5-lipoxygenase activity, which inhibitory activity has been associated with antiallergy, antiinflammatory and antihyperproliferative activity. The compounds of the invention are thus useful for the treatment of allergic diseases such as asthma, and inflammatory diseases such as arthritis, bursitis, tendonitis, gout and inflammatory bowel disease, as well as hyperproliferative skin diseases. "Hyperproliferative skin disease" means any condition a sympton of which is accelerated skin cell production, flaking, scales or papular lesions, including, for example, psoriasis, eczema, dandruff and the like. 5-lipoxygenase inhibition by the compounds of the invention may be demonstrated by the procedure described below.

5-Lipoxygenase Assay

Use the interleukin-3-dependent murine mast cell clone, MC-9, to test the effects of representative compounds of the invention on lipoxygenase activity. Grow the MC-9 cell line in suspension culture (0.4 to 1.2×10⁶ cells/ml) in RPMI 1640 medium (Gibco) with 10% fetal bovine serum (Hyclone) and 2–5% concanavalin-A conditioned supernatant (Musch et. al., (1985) Prostagandins 29, 405–4307). Harvest the cells, wash them twice by centrifugation, and resuspend them in a Ca++-free HEPES buffer (25 mM HEPES, 125 mM NaCl, 2.5 mMKCl, 0.7 mM MgCl₂0.5 mM EDTA and 10 mM glucose at pH 7.4).

Preincubate MC-9 cells (0.39 ml at 7.5×10⁶ cells/ml) without or with test compound dissolved in dimethylsulfoxide (DMSO) vehicle (to final volume 1 ml) for 4 minutes then incubate for 5 minutes with [¹⁴C]-arachidonic acid (Amersham, 59 Ci/mole) at a 9 mM final concentration, and A23187 (Calbiochem) at a 1 mM final concentration in 10 ml of water:ethanol (9:1). Stop the reaction by addition of methanol (0.4 ml), and remove cellular debris by centrifugation. Run aliquots (250 ml) of the incubations on a Waters two-pump HPLC system fitted with a Waters radial compression column (C18, 10 micron, 8×100 mm, micro-Bondapak) and C18 "Guard Pak". Initially elute the column at 3 ml/min with water:methanol:acetic acid (67:33:0.08) containing 1 mM EDTA adjusted to pH 6.0 with ammonium hydroxide (Pump A). At 4 minutes, establish a linear gradient to reach 100% methanol (Pump B) at 9 minutes. Between 13 and 14 minutes, exchange for the initial eluting solvent and by 19 minutes the column will be reequilibrated for the next sample. Analyze the effluent by a continuous flow radioactivity monitor (model ROMONA-D) interfaced with a Hewlett Packard Lab Automation System for quantitation of radioactive products.

These products are predominantly leukotriene C4 (LTC4), which elutes at 6 minutes, and 5-hydroxyeicosatetraenoic acid (5-HETE), which elutes at 11 minutes (Musch et. al., supra). Use the results with and without test compound to calculate percent inhibition of LTC4 and 5-HETE production for representative compounds of the invention as shown in Table 1 below. Doses in table 1 are 50 µM unless otherwise noted.

TABLE 1

| Compound | 5-Lipoxygenase Activity % Inhibition at 50 µM |
|---|---|
| 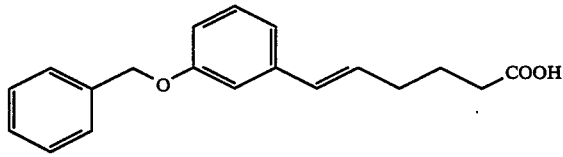 | 84 |
| 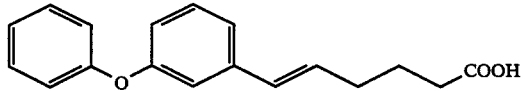 | 74 |
| 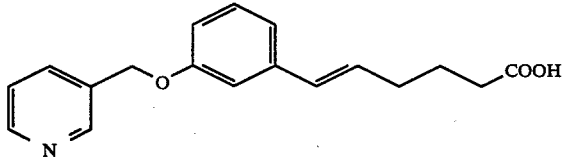 | 7 |
| 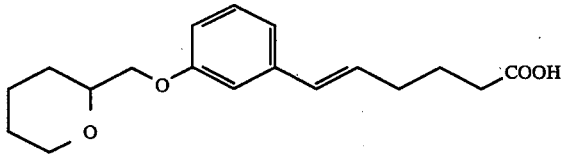 | 23 |
| 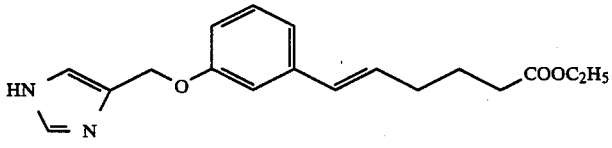 | 89 |
| 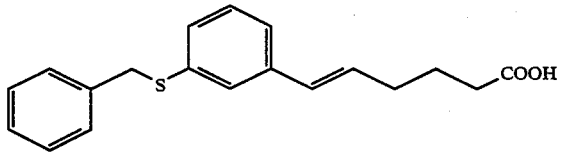 | 0* |
| 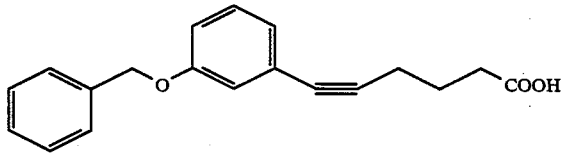 | 80 |
| 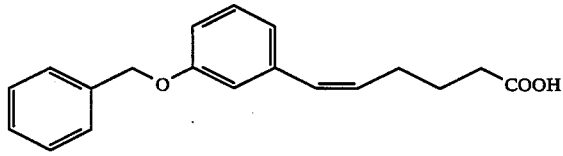 | 89 |

TABLE 1-continued

| Compound | 5-Lipoxygenase Activity % Inhibition at 50 μM |
|---|---|
| 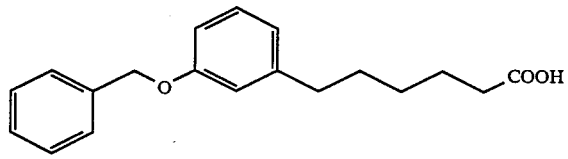 | 80 |

*expected to show activity at a higher dose

The active compounds can be administered orally, topically, parenterally, or by oral or nasal inhalation. The preferred mode of administration is orally or intravenously.

Formulations for topical application, e.g., for use in treating hyperproliferative skin disease, may include the liquid forms, creams, aerosols, sprays, dusts, powders, lotions and ointments which are prepared by combining an active ingredient according to this invention with conventional pharmaceutical diluents and carriers commonly used in topical dry, liquid, cream and aerosol formulations. Ointment and creams may, for example, be formulated with an aqueous or oily base with the addition of suitable thickening and/or gelling agents. For example, such bases may include water and/or and oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

The topical pharmaceutical compositions according to the invention may also include one or more preservatives or bacteriostatic agents, e.g., methyl hydroxybenzoate, propyl hydroxybenzoate, chlorocresol, benzalkonium chlorides, etc.

The topical pharmaceutical compositions according to the invention may also contain other active ingredients such as antimicrobial agents, particularly antibiotics, anesthetics, analgesics and antipruritic agents.

Lotions may be formulations with an aqueous or oily base and will, in general, also include one or more of stabilizing agents, emulsifying agents, dispersing agents, suspending agents, thickening agents, coloring agents, perfumes and the like.

Powders may be formed with the aid of any suitable powder base, e.g., talc, lactose, starch, etc. Drops may be formulated with an aqueous base or non-aqueous base also comprising one or more dispersing agents, suspending agents, solubilizing agents, etc.

The compounds can be administered in conventional oral dosage forms such as capsules, tablets, pills, powders, suspensions or solutions prepared with conventional pharmaceutically acceptable excipients and additives, using conventional techniques. Parenteral preparations, i.e., sterile solutions or suspensions are also made by conventional means. Inhalation administration can be in the form of a nasal or oral spray. Insufflation is also contemplated.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may comprise from about 5 to about 70 percent active ingredient. Suitable solid carriers are known in the art, e.g., magnesium carbonate, magnesium stearate, talc, sugar, lactose. Tablets, powders, cachets and capsules can be used as solid dosage forms suitable for oral administration.

Liquid form preparations include solutions, suspensions and emulsions. As an example may be mentioned water or water-propylene glycol solutions for parenteral injection.

Liquid form preparation may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, muliple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain in addition to the active material, flavorants, colorants, stabilizers, buffers, artificial and natural sweeteners, dispersants thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

For preparing suppositories, a low melting wax such as mixture of fatty acid glycerides or cocoa buffer is first melted, and the active ingredients is dispersed homogeneously therein as by stirring. The molten homogeneous mixture is then poured into convenient sized molds, allowed to cool and thereby solidify.

Preferably, the pharmaceutical preparation is in unit dosage form, in such form, the preparation is subdivided into unit doses containing appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

When administered topically for the treatment of hyperproliferative skin disease, the amount of compound varies widely with the concentration of active ingredient applied to the affected area. When administered orally, the compounds of formula I are effective for the treatment of hyperproliferative skin disease at doses ranging from about 0.1 mg to about 1000 mg. When administered parenterally, the compounds of formula I are effective for the treatment of hyperproliferative skin disease in doses ranging from about 0.1 mg/kg body weight to about 10 mg/kg body weight, which may be administered in divided doses.

When used orally or parenterally for the treatment of inflammation, the compounds of the invention can be administered in an amount ranging from about 0.1 mg/kg body weight to about 100 mg/kg body weight, preferably from about 0.1 mg/kg body weight to about 25 mg/kg body weight per day. A typical recommended dosage regimen is oral administration of from 10 mg/day to 1500 mg/day, preferably 10 mg/day to 750 mg/day, in two to four divided doses to achieve relief of the inflammation symptoms.

The compounds can be administered by any conventional mode of administration for the treatment of allergic reactions employing an effective amount of a compound of formula I. For example, when administered orally, appropriate doses are from about 1 mg/kg body weight to about 100 mg/kg body weight; when administered parenterally, e.g., intravenously, the compounds can be administered at dosages of from about 0.1 mg/kg body weight to about 10 mg/kg body weight; when administered by inhalation (aerosol or nebulizer) the compounds can be administered at doses of from about 0.1 mg to 20 mg per puff, one to four puffs can be taken every 4 hours.

The following examples are intended to illustrate the invention without limiting it in any way.

EXAMPLE 1

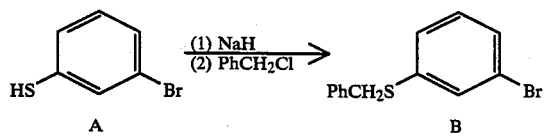

A. To a mixture of 0.48 grams of NaH (50% oil dispension, washed three times with hexane) in 5 ml of dry DMF was added 1.1 ml of m-bromothiophenol (10 mole). After 1 hour of stirring under $N_2$, a solution of 1.15 ml of benzyl chloride (10 mole) in 4 ml of dry DMF was added dropwise over 30 minutes. The resulting solution was stirred for an additional ½ hour then it was quenched by water and extracted with hexane. The hexane solution was washed with water, brine, dried over $MgSO_4$, and concentrated to give 2.49 g (88% yield) of the desired product of formula B.

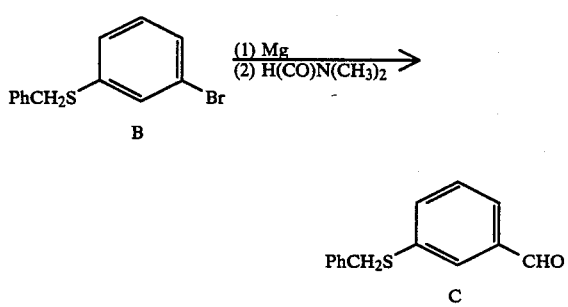

B. To a mixture of 0.122 g of Mg turnings (5 mmole) in 1 ml of dry THF was added 0.5 ml of a solution of a compound of formula B above (prepared by dissolving 1.396 g of the compound B in 5 ml of THF). The stirred mixture was heated to reflux, the remaining 4.5 ml of the solution containing compound B was added dropwise over ½ hour, the reaction mixture was stirred for another 4 hours, and then it was cooled to room temperature. A solution of 0.39 ml of DMF (5 mmole) in 0.5 ml of THF was added dropwise to the above Grignard reagent. After completing addition, the reaction mixture was stirred for 3 hours at room temperature, then it was quenched with saturated $NH_4Cl$ solution and extracted with ether. The ether extracts were dried over $MgSO_4$ and concentrated to give a yellow oil, which was purified by flash chromatography on $SiO_2$ to give 0.64 g (56% yield) of the product of formula C above.

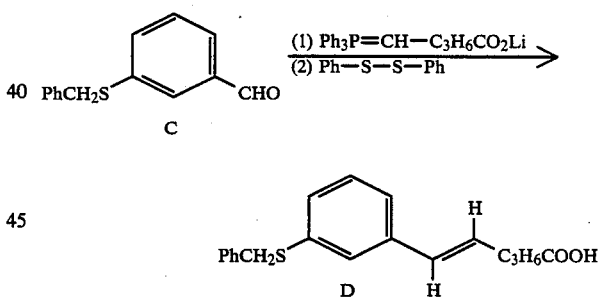

C. To a mixture of 0.64 g of (4-carboxybutyl)-triphenyl phosphonium bromide (1.45 mmole) in 3 ml of anhydrous tetrahydrofuran (THF) was added 2.89 ml of 1M lithium bis(trimethylsilyl)amide (2.89 mmole) the resulting deep orange-red solution was stirred at room temperature for ½ hour. A solution of 0.269 g of a compound of formula C (1.45 mmole) in 1 ml of dry THF was added. After 1 hour of stirring at room temperature, the reaction mixture was quenched by water and extracted with diethyl ether. The aqueous solution was cooled to 0° C., acidified to pH of about 2, and extracted with ethyl acetate (EtOAc), the combined EtOAc extracts were dried over anhydrous $MgSO_4$ and concentrated. The residue was purified by flash chromatography on $SiO_2$ (eluting first with $CH_2Cl_2$ then with 95:5 $CH_2Cl_2$/EtOAc and finally with 85:15 $CH_2Cl_2$/EtOAc) to give 0.30 g (74% yield) of product (cis plus trans). The trans product of formula D could be obtained (0.25 g; 61% yield) from the cis plus trans isomers mixture either by crystallization in MeOH/H₂O or by irradiation of the above product (cis plus trans) in 25 ml of benzene with visible light for 15 hours in the presence of 18 mg of Ph-S-S-Ph, wherein Ph represents a phenyl group. M.p. of Compound D=44°-47° C.

EXAMPLE 2

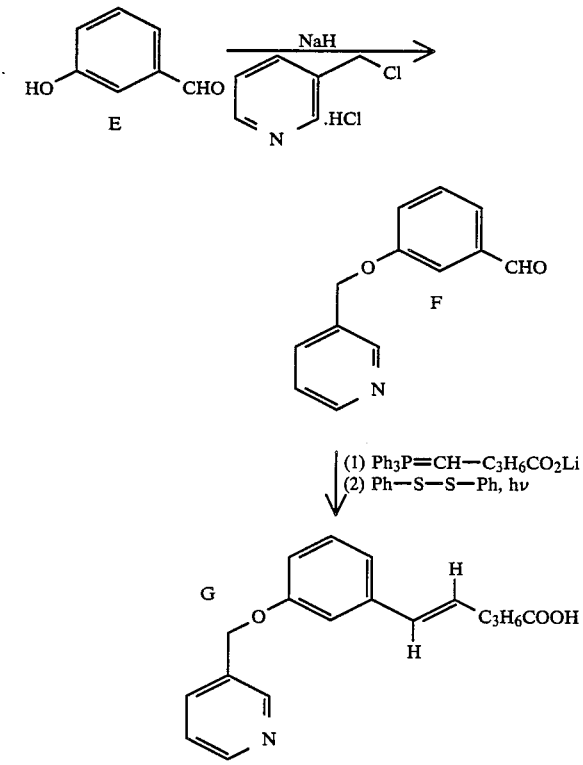

By a procedure similar to Example 1A above, compound E was converted to F in 28% yield. By a procedure similar to Example 1C above, compound G was prepared from Compound F in 46% yield, m.p.=90°-93° C.

EXAMPLE 3

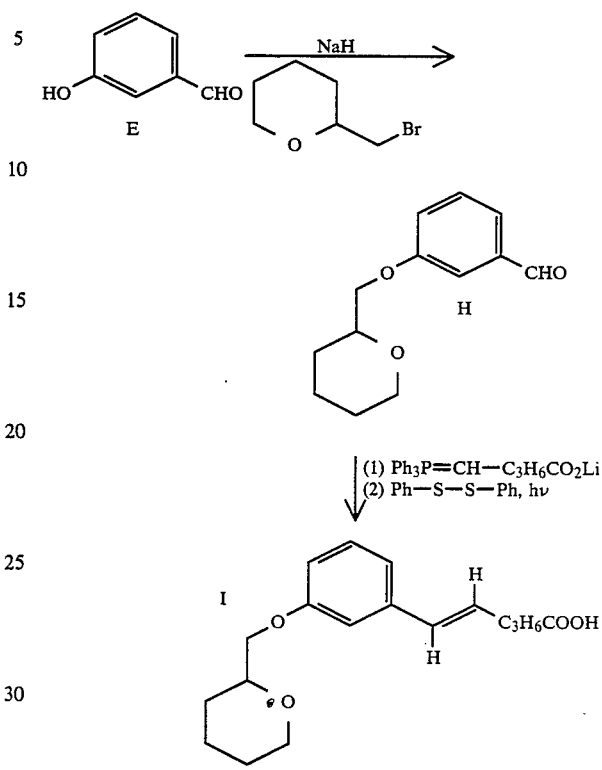

By a procedure similar to Example 1A and 1C above, compound H and compound I were prepared from compounds E and H in 22% and 90% yield respectively. M.p. of compound I=46°-48.5° C.

EXAMPLE 4

Compounds of formula J to M were prepared by basically the same the procedure described above in Example 1C using the starting reactant in the left hand column below.

REACTANT ⟶ PRODUCT (% yield; melting point)

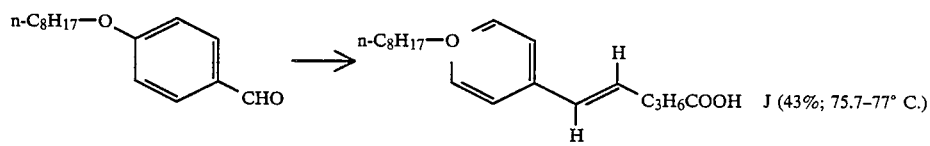
J (43%; 75.7-77° C.)

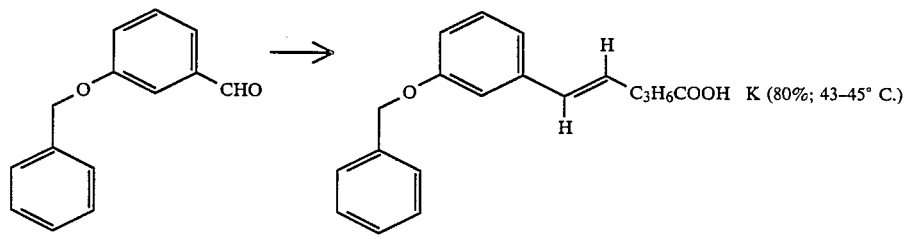
K (80%; 43-45° C.)

-continued

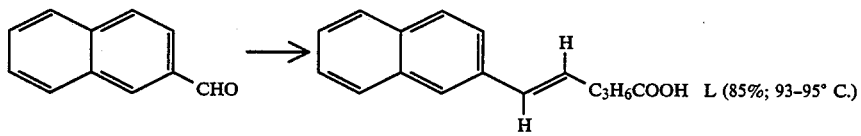 L (85%; 93-95° C.)

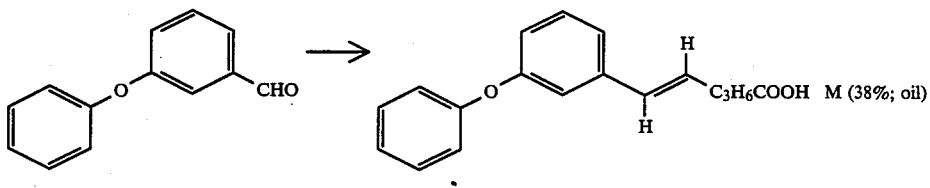 M (38%; oil)

EXAMPLE 5

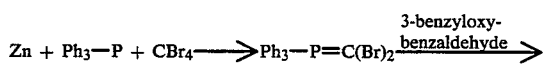

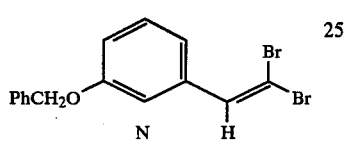

A. To a mixture of 15.74 g of Ph₃P (60 mmole) and 3.93 g of Zn dust (60 mmole) in 120 ml of CH₂Cl₂ was added 19.9 g of CBr₄ (60 mmole) portionwise. The resulting mixture was stirred at room temperature for 23 hours, then a solution of 6.36 g of 3-benzyloxy-benzaldehyde (30 mmol) in 15 ml of CH₂Cl₂ was added dropwise. The reaction mixture was stirred at room temperature for 2 hour, then it was filtered. The filtrate was concentrated, the residue was purified by flash chromatography to give 6.9 g (62% yield) of the desired product of formula N which was used directly to the next step.

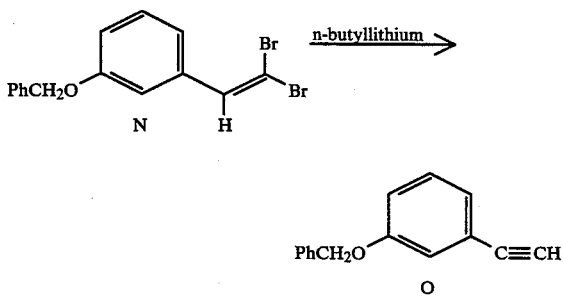

B. To a solution of 6.9 g of the 1,1-dibromo olefin of formula N in 100 ml of dry THF was added 2 equivalents of n-butyl lithium (24.2 ml of 1.55M BuLi) at −78 C. The reaction mixture was stirred at −78 C. The reaction mixture was stirred at "78° C. for 1 hour and at room temperature for another 1 hour, then it was quenched with water. The organic layer was separated, washed with brine, dried over MgSO₄ and concentrated. The residue was purified by flash chromatography on SiO₂ to give 1.5 g (39% yield) of the desired product of formula O, which was used directly to the next step.

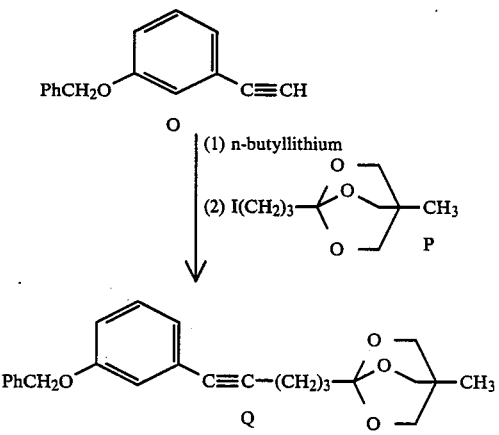

C. To a solution of 0.83 g of the phenyl-acetylene of formula O (4 mmole) in 16 ml of dry THF was added 2.67 ml of 1.5N n-butyl lithium (4 mmole) at −78° C. under N₂. After 1 hour of stirring at −78° C., a solution of 1.09 g (3.65 mmole) of cyclic orthoester of formula P (which can be prepared as described in Tetrahedron Letters, 25(45): 5115(1984)) in 6 ml of 1:1 THF/hexamethylphosphoramide was added dropwise. The reaction mixture was stirred at −78° C. for 10 minutes and at 0° C. for 1 hour, then was quenched with water and extracted with diethyl ether. The ether extracts were washed with water and brine, dried over anhydrous NaHCO₃ and then concentrated. The residue was purified by flash chromatography on SiO₂ (silica gel was deactivated with triethylamine) to give 1.24 g (90% yield) of product (light yellow crystals) of formula Q above.

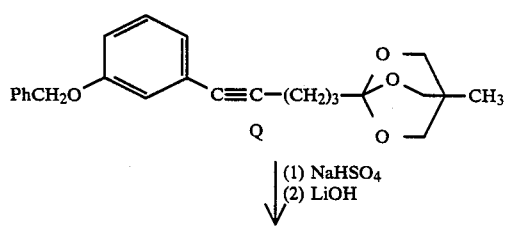

-continued

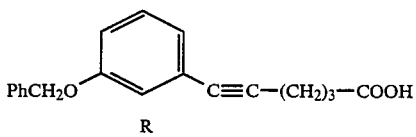

D. To a solution of 0.12 g of the acetylene orthoester of formula Q above in 6 ml of 1:1 1,2-dimethoxyethane/water was added a small crystal of NaHSO₄.H₂O at 0° C. This give a solution of about pH 3. After ½ hour of stirring at 0° C., a solution of 2 ml of 3N LiOH was added, the reaction mixture was stirred at room temperature for 50 minutes, then it was acidified to pH of about 3 with NaHSO₄ solution. The resulting solution was extracted with EtOAc. The EtOAc extracts were washed with brine, dried over anhydrous MgSO₄, and concentrated. The residue was purified by flash chromatography on SiO₂ to give 0.098 g of product which was recrystallized from CH₃OH and water to give 90 mg (95% yield) of white crystals of formula R above, m.p.=68°-70° C.

EXAMPLE 6

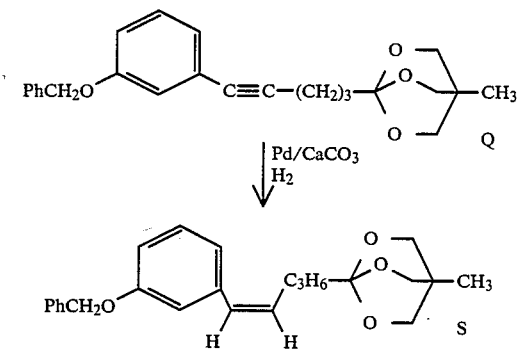

A. A mixture of 0.25 g of the acetylene orthoester of formula Q above (0.66 mmole), 25 mg of Lindlar catalyst (PD/CaCO₃) and 8 ml of triethylamine in 4 ml of dry THF was stirred at room temperature under 1 atmosphere of hydrogen for 5 hours (the reaction was monitored by TLC). The reaction mixture was filtered through a pad of celite and the filtrate was concentrated to give 0.0228 g of the cis olefin (90% yield) of formula S above, which was used directly for the next step B.

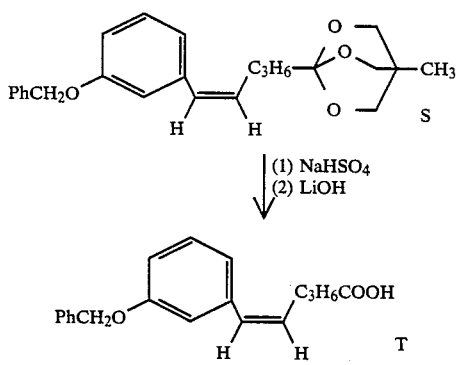

B. By essentially the same procedure as described in Example E 5D above, substituing the olefin of formula S for the acetylene of formula Q, the corresponding olefin of formula T above was obtained, m.p.=44°-47° C.

EXAMPLE 7

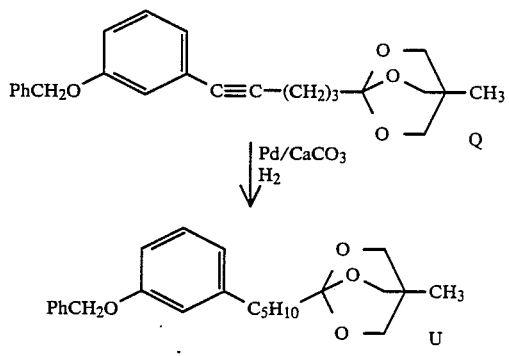

A. A mixture of 0.25 g of the acetylene orthoester of formula Q above, 100 mg of Lindlar catalyst and 0.5 ml of triethylamine in 5 ml of dry THF was stirred at room temperature under one atmosphere of hydrogen for 21 hours. The mixture was filtered through a pad of celite, and the filtrate was concentrated to give 0.23 g of saturated product (90% yield) of formula U above, which was used directly in the next step B.

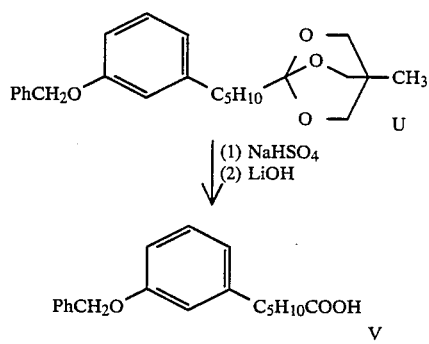

B. By essentially the same procedure as described in Example 5D above, substituting the saturated compound of formula U for the acetylene of formula Q in Example 5, the corresponding carboxylic acid of formula V was obtained, m.p.=75°-76° C.

EXAMPLE 8

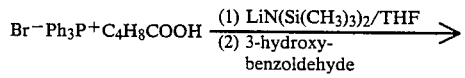

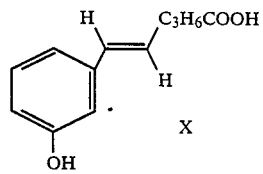

To a mixture of 159 g of (4-carboxybutyl)-triphenyl phosphonium bromide in 48 ml of anhydrous THF was added 790 ml of 1M lithium bis(trimethylsilyl)amide under nitrogen with stirring over 10 minutes at room temperature. The resulting solution was stirred for another 30 minutes, then a solution of 21.9 g of 3-hydroxybenzaldehyde in 70 ml of anhydrous THF was added with precipitates being generated immediately. The mixture was stirred at room temperature for 1 hour, then it was quenched with water (900 ml) and diethyl ether (900 ml). The organic phase was washed with water (500 ml), the combine aqueous solutions were washed with EtOAc three times (3×800 ml) until all the 3-hydroxybenzaldehyde had been removed. The aqueous solution was then cooled to 0° C. and acidified with 10% HCl to a pH of about 2. The resulting solution was then extracted with EtOAc (2×900 ml), the combined EtOAc extracts were rinsed with brine (saturated NaCl solution), dried over anhydrous MgSO$_4$ and concentrated. The residue was purified by flash chromatography on SiO$_2$ (eluted with 10% ether in CH$_2$Cl$_2$ in the presence of 0.1% acetic acid) to give 29.8 g of very pale yellow precipitate, which was recrystalized with CH$_2$Cl$_2$ to yield 23.85 g (65% yield) of the pure trans olefin of formula X above.

EXAMPLE 9

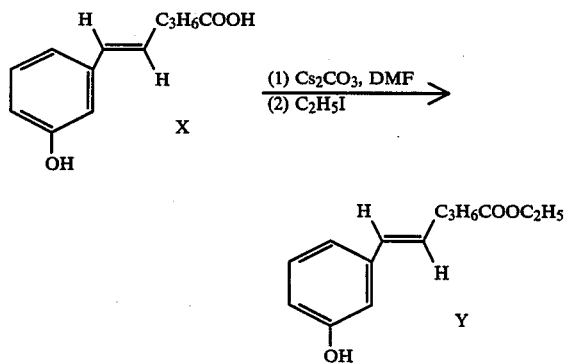

To a solution of 28.2 g of the trans olefin of formula X above in 135 ml of anhydrous DMF was added 22.41 g of Cs$_2$CO$_3$ at 0° C. under nitrogen. The mixture was stirred at 0° C. for 5 minutes, then 11.55 ml of iodoethane was added dropwise. After finishing addition of the iodoethane, the cooling bath was removed and the resulting mixture was stirred at room temperature under nitrogen for 41 hours. The reaction mixture was then quenched with water and extracted with diethyl ether. The ether extracts were washed with brine, dried over anhydrous MgSO$_4$ and concentrated. The residue was purified by flash chromatography on SiO$_2$ (eluting solvent was CH$_2$Cl$_2$ until all the nonpolar material came out, then polarity was increased to 1% either in CH$_2$Cl$_2$, and finally to 8% ether in CH$_2$Cl$_2$) to give 29 g of pure product (90% yield) of formula Y above.

EXAMPLE 10

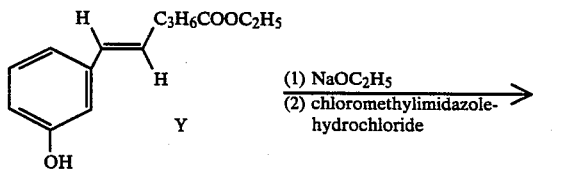

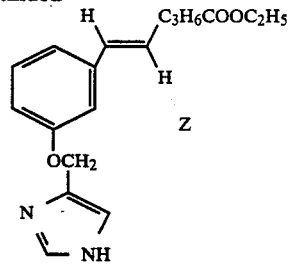

Sodium (2.91 g) was added to a solution of 140 ml of absolute ethanol in a flask equipped with a condenser having a nitrogen inlet, and with a dropping funnel. When all the sodium was dissolved and the temperature of the solution was cooled to room temperature. A solution of 29.48 g of the compound of formula Y above in 65 ml of absolute ethanol was added dropwise. The resulting solution was allowed to stir at room temperature for 2 hours, then it was cooled to 0° C. (ice-salt bath). A solution of 9.68 g of 4-chloromethylimidazole hydrochloride in 95 ml of absolute ethanol was then added slowly (temperature kept below 5° C.) to the above reaction mixture at 0° C. The resulting mixture was stirred an additional 6 hours at room temperature, and then it was filtered and the filtrate was concentrated. The residue was cooled in an ice water bath and 63 ml of 3N HCl solution was added. The resulting solution was extracted with diethyl ether (2×70 ml) to remove the unreacted starting material of formula Y. The aqueous solution was neutralized by addition of 158 ml of saturated NaHCO$_3$ solution at 0° C., then it was extracted with ethyl acetate (3×100 ml). The combined ethyl acetate extracts were dried over NaHCO$_3$, filtered and concentrated. The residue was purified by flash chromatography on SiO$_2$ (eluting solvent CH$_2$Cl$_2$, the polarity of which was increased gradually to either, and finally to EtOAc). Two fractions were collected. The nonpolar compound is the starting material of formula Y above, and the polar compound is the desired product of formula Z above, 11.9 g (60% yield), m.p.=70.5°-72° C.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the formula

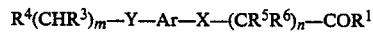

or a pharmaceutically acceptable salt thereof, wherein m represents an integer of from 0 to 4;

n represents an integer of from 2 to 6:

Ar represents

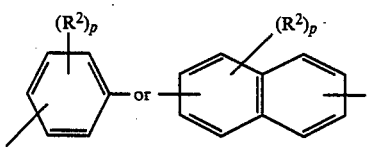

p is 0, 1 or 2;

X represents —C≡C—, —CH=CH— or —CH$_2$—CH$_2$—

Y represents O, S, NR$^7$ or a covalent bond;

R$^1$ represents alkoxy, OH or N(R$^7$)$_2$;

each R$^2$ independently represents a substituent selected from halo, alkyl, alkoxy, CN, OH, NO$_2$, CF$_3$ or cycloalkyl;

R$^3$ represents H, alkyl, alkenyl, alkynyl, alkoxy, or alkylthio, with the proviso that if Y is O, S or NR$^7$, R$^3$ is not alkoxy or alkylthio on the carbon atom adjacent to Y;

R$^4$ represents H, alkyl, alkenyl, alkynyl or a cyclic group selected from:

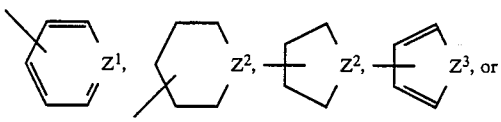

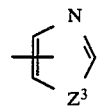

wherein Z$^1$ is N, CH or CR$^2$, Z$^2$ is CHR$^7$, O, S or NR$^7$ and Z$^3$ represents NR$^7$, S or O; with the proviso that when M is O and Y is a covalent bond, R4 is not alkyl;

R$^5$ and R$^6$ may be the same or different and each independently represents H, alkyl, alkoxy, or alkylthio, with the proviso that R$^5$ and R$^6$ are not both alkoxy and/or alkylthio on the same carbon atom; and each R$^7$ is independently selected from H or alkyl.

2. A compound according to claim 1, wherein R$^4$ is a cyclic group selected from

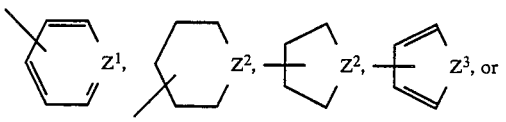

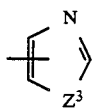

wherein R$^2$, Z$^1$, Z$^2$ and Z$^3$ are as defined in claim 1.

3. A compound according to claim 2, wherein R$^2$ is selected from H, OH, alkoxy or halo.

4. A compound according to claim 3, wherein R$^5$ and R$^6$ are independently selected from H or alkyl.

5. A compound according to claim 4, wherein R$^5$ and R$^6$ are both H.

6. A compound according to claim 5, wherein n is an integer of from 2 to 4.

7. A compound according to claim 6, wherein n is 3.

8. A compound according to claim 6, wherein m is 0, 1 or 2.

9. A compound according to claim 8, wherein R$^3$ is H or alkyl.

10. A compound according to claim 9, wherein X is

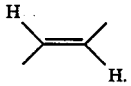

11. A compound according to claim 10, wherein Y is O.

12. A compound of formula

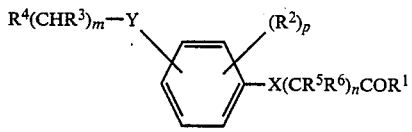

or a pharmaceutically acceptable salt thereof, wherein m, n, p, X, Y, R$^1$, R$^2$, R$^3$, R$^4$, R$^5$ and R$^6$ are as defined in claim 1.

13. A compound according to claim 1 having the name:
6-(4-octadecoxyphenyl)-5-hexenoic acid;
6-[3-(phenylmethoxy)phenyl]-5-hexenoic acid;
6-(2-naphthalenyl)-5-hexenoic acid;
6-(3-phenoxyphenyl)-5-hexenoic acid;
6-[3-(3-pyridinylmethoxy)phenyl]-5-hexenoic acid;
6-[3-[(tetrahydro-2H-pyran-2-yl)methoxy]phenyl]-5-hexenoic acid;
Ethyl 6-[3-(1H-imidazol-4-ylmethoxy)phenyl]-5-hexenoate;
6-[3-[(phenylmethyl)thio]phenyl]-5-hexenoic acid;
6-[3-(phenylmethoxy)phenyl]-5-hexynoic acid; or
3-(phenylmethoxy)benzeneheptanoic acid.

14. A compound according to claim 1 having the name Ethyl-6-[3-(1H-imidazol-4-ylmethoxy)phenyl]-5-hexenoate.

15. A pharmaceutical composition comprising an effective amount of a compound as defined in claim 1 in combination with a pharmaceutically acceptable carrier.

16. A method for treating inflammation in a mammal comprising administering to said mammal an antinflammatory effective amount of a compound as defined in claim 1.

17. A method for treating allergy in a mammal comprising administering to said mammal an anti-allergic effective amount of a compound as defined in claim 1.

18. A method for treating hyperproliferative skin disease in a mammal comprising administering to said mammal an effective amount of a compound as defined in claim 1.

* * * * *